US00PP21782P2

(12) United States Plant Patent
Smith

(10) Patent No.: US PP21,782 P2
(45) Date of Patent: Mar. 15, 2011

(54) ***CHRYSANTHEMUM* PLANT NAMED 'FROSTY YOCHERYL**

(50) Latin Name: *Chrysanthemum×morifolium*
Varietal Denomination: Frosty Yocheryl

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/590,885

(22) Filed: Nov. 16, 2009

(51) Int. Cl.
*A01H 5/00* (2006.01)

(52) U.S. Cl. ..... Plt./288

(58) Field of Classification Search ..... Plt./288
See application file for complete search history.

(56) References Cited

U.S. PATENT DOCUMENTS

PP8,943 P * 10/1994 Olesen et al. ..... Plt./121
PP18,924 P2 * 6/2008 Smith ..... Plt./288

* cited by examiner

*Primary Examiner*—Wendy Haas
(74) *Attorney, Agent, or Firm*—S. Matthew Edwards

(57) ABSTRACT

A new *Chrysanthemum* plant named 'Frosty Yocheryl,' particularly distinguished by the medium sized inflorescences with white colored mature ray florets, good floriferousness, dark green foliage with a well mounded plant habit, and a natural flowering season of early October.

1 Drawing Sheet

Latin name of the genus and species of the plant claimed: *Chrysanthemum×morifolium.*

Varietal denomination: 'Frosty Yocheryl'.

BACKGROUND OF THE NEW PLANT

The present invention comprises a new *Chrysanthemum*, botanically known as *Chrysanthemum×morifolium*, and hereinafter referred to by the variety name 'Frosty Yocheryl.'

'Frosty Yocheryl' is a product of a planned breeding program. The new cultivar has medium sized inflorescences with white colored mature ray florets, good floriferousness, dark green foliage with a well mounded plant habit, and a natural flowering season of early October.

'Frosty Yocheryl' originates as a natural whole plant mutation of 'Cool Yocheryl,' U.S. Plant Pat. No. 8,943. 'Frosty Yocheryl' was discovered and selected by the inventor as a single flowering plant within a population of the parent cultivar in a controlled breeding program in Alva, Fla. in November 2006. The parent cultivar 'Cool Yocheryl' has more pink over-tones on a white flower, taller plant habit and has a few days faster flowering response.

The first act of asexual reproduction of 'Frosty Yocheryl' was accomplished when vegetative cuttings were propagated from the initial selection in November 2006 in a controlled environment in Alva, Fla.

BRIEF SUMMARY OF INVENTION

Horticultural examination of plants grown from cuttings of the plant initiated in November 2006 and continuing thereafter, has demonstrated that the combination of characteristics as herein disclosed for 'Frosty Yocheryl' are firmly fixed and are retained through successive generations of asexual reproduction.

'Frosty Yocheryl' has not been observed under all possible environmental conditions. The phenotype may vary significantly with variations in environment such as temperature, light intensity and day length.

Plant Breeder's Rights for this cultivar were applied for in the European Union on Nov. 28, 2008 and in Canada on Oct. 30, 2009. 'Frosty Yocheryl' has not been made publicly available more than one year prior to the filing of this application.

The following traits have been repeatedly observed and are determined to be basic characteristics of the new variety. The combination of these characteristics distinguishes this *Chrysanthemum* as a new and distinct variety

BRIEF DESCRIPTION OF THE PHOTOGRAPHS

The accompanying photographic drawing shows typical flower and foliage characteristics of 'Frosty Yocheryl' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken outdoors in Gilroy, Calif. in late October 2009. These plants were approximately 12-14 weeks of age. The plants were propagated in Alva, Fla., then shipped to California at about 3-4 weeks of age, potted up and set outdoors in the trial.

Color references are made to The Royal Horticultural Society Colour Chart (R.H.S.) 2001.

TABLE 1

DIFFERENCES BETWEEN THE NEW VARIETY 'FROSTY YOCHERYL' AND A SIMILAR VARIETY

| | 'Frosty Yocheryl' | 'Yowilma' (U.S. Plant Pat. No. 18,924) |
|---|---|---|
| Plant height: | Slightly shorter | Slightly taller |
| Plant habit: | More compact and rounded | Less compact and not so uniformly rounded |
| Quantity of disc florets | More | Fewer |

Plant:
- *Form, growth and habit.*—Herbaceous decorative garden-type. Stems upright and outwardly spreading, freely branching.
- *Plant height.*—9-10 cm.
- *Plant height (inflorescence included).*—14-15 cm.
- *Plant width.*—18-19 cm.
- *Garden performance and tolerance to weather.*—Very good.
- *Crop time to flowering.*—About 10-12 weeks.

Roots:
- *Number of days to initiate roots.*—4-6 days at about 22 degrees C.
- *Number of days to produce a rooted cutting.*—7-10 days at 22 degrees C.
- *Type.*—Fine, fibrous, free branching.
- *Color.*—RHS N155B but whiter.

Foliage:
- *Arrangement.*—Alternate.
- *Immature, leaf color, upper surface.*—Closest to RHS 147A.
- *Immature, leaf color, lower surface.*—RHS 147B but a little darker.
- *Mature, leaf color, upper surface.*—Closest to RHS 147A.
- *Mature, leaf color, lower surface.*—RHS 147B but a little darker.
- *Length.*—5-5.2 cm.
- *Width.*—4.5-5.3 cm.
- *Shape.*—Ovate.
- *Base shape.*—Attenuate.
- *Apex shape.*—Acute to obtuse.
- *Margin.*—Palmately lobed; slightly incised, serrate.
- *Texture, upper surface.*—Bifid T-shaped hairs.
- *Texture, lower surface.*—Bifid T-shaped hairs.
- *Color of veins, upper surface.*—RHS 144A.
- *Color of veins, lower surface.*—RHS 144A.
- *Petiole color.*—RHS 144A.
- *Length.*—0.8-1.0 cm.
- *Diameter.*—0.3 cm.
- *Texture.*—Bifid T-shaped hairs.

Stem:
- *Quantity of main branches per plant.*—About 8.
- *Quantity of leaves per branch.*—4-6.
- *Color of stem.*—RHS 147C.
- *Length of stem.*—10-12 cm.
- *Diameter.*—0.3-0.4 cm.
- *Length of internodes.*—0.5-1.5 cm.
- *Texture.*—Bifid T-shaped hairs.
- *Color of peduncle.*—RHS 147C.
- *Length of peduncle.*—3.8-4.5 cm.
- *Peduncle diameter.*—0.2 cm.
- *Texture.*—Bifid T-shaped hairs.

Inflorescence:
- *Type.*—Composite type, solitary inflorescences (decorative-type) borne terminally above foliage, ray florets arranged acropetally on a capitulum.
- *Blooming habit.*—Natural season flowering about early October.
- *Quantity of inflorescences per plant.*—20-23 open flowers and about 40-50 buds.
- *Quantity of inflorescences per lateral stem.*—4-5.
- *Lastingness of individual blooms on the plant.*—About 4 weeks.
- *Fragrance.*—Slightly spicy.

Bud (just before opening/showing color):
- *Color.*—Closest to RHS 8C with a brighter apex.
- *Length.*—0.8-0.9 cm.
- *Width.*—1.0-1.3 cm.
- *Shape.*—Oblate.

Immature inflorescence:
- *Diameter.*—3.5-3.9 cm.
- *Color of ray florets, upper surface.*—Closest to RHS 8C maturing to RHS 155B but whiter.
- *Color of ray florets, lower surface.*—RHS 155B but whiter.

Mature inflorescence:
- *Diameter.*—5.5 cm.
- *Depth.*—1.5 cm.
- *Total diameter of 'disc'.*—Not showing at the time.
- *Recepticle height.*—0.4 cm.
- *Recepticle diameter.*—0.7 cm.

Ray florets:
- *Average quantity of florets.*—About 200 in numerous whorls.
- *Color of florets, upper surface.*—RHS N155B but whiter.
- *Color of florets, lower surface.*—RHS N155B but whiter.
- *Length.*—1.7-2.4 cm.
- *Width.*—0.5-0.6 cm.
- *Shape.*—Elliptical.
- *Apex shape.*—Praemorse.
- *Margin.*—Entire.
- *Texture, upper surface.*—Papillose.
- *Texture, lower surface.*—Papillose.

Disc florets:
- *Average quantity of florets.*—6-20.
- *Color of florets.*—RHS 9A with RHS 155D basally.
- *Length.*—0.3 cm.
- *Width.*—0.1 cm.
- *Shape.*—Tubular, elongated.
- *Apex shape.*—Acute, 5 pointed.

Phyllaries:
- *Quantity.*—20-30.
- *Color, upper surface.*—RHS 146B with brown papery margins of RHS 200A.
- *Color, lower surface.*—RHS 146B.
- *Length.*—0.3-0.4 cm.
- *Width.*—0.1-0.2 cm.
- *Shape.*—Lanceolate.
- *Apex shape.*—Acute.
- *Based.*—Fused.
- *Margins.*—Entire.
- *Texture, upper surface.*—Bifid T-shaped hairs.
- *Texture, lower surface.*—Bifid T-shaped hairs.

Reproductive organs:
- *Pistil.*—1.
- *Length.*—0.4 cm.
- *Style color.*—RHS 1C.
- *Style length.*—0.2-0.3 cm.
- *Stigma color.*—RHS 5A.
- *Stigma shape.*—Bi-parted.
- *Ovary color.*—RHS 155C.
- *Stamens.*—1.
- *Color of filaments.*—RHS 1C.
- *Length filaments.*—0.2 cm.
- *Anther color.*—RHS 3A.

*Anther length.*—0.1 cm.

*Anther shape.*—Oblong.

*Color and amount of pollen.*—Not observed.

*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Frosty Yocheryl,' substantially as illustrated and described herein.

* * * * *

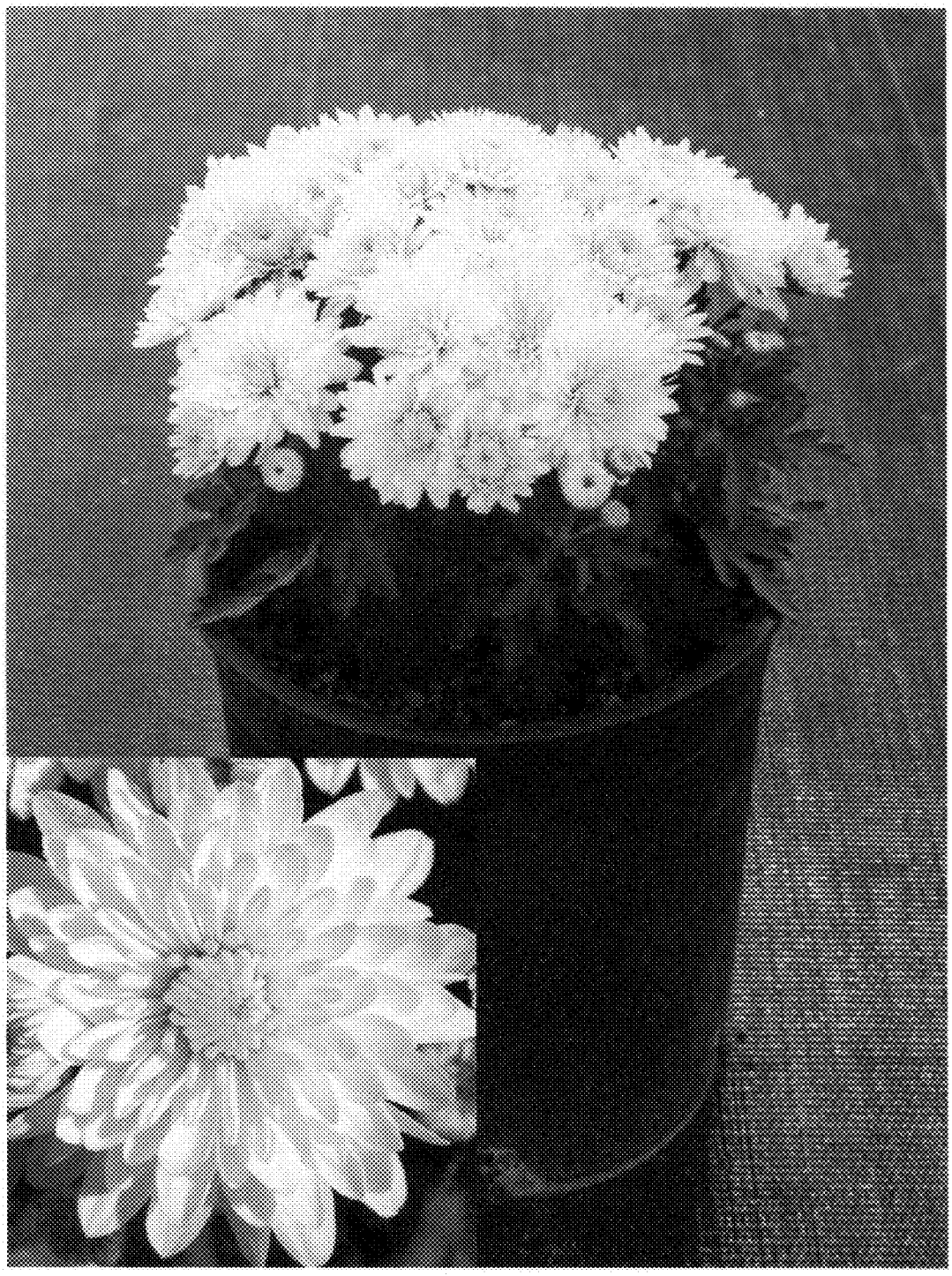

UNITED STATES PATENT AND TRADEMARK OFFICE

CERTIFICATE OF CORRECTION

PATENT NO. : PP21,782 P2
APPLICATION NO. : 12/590885
DATED : March 15, 2011
INVENTOR(S) : Smith It is certified that error appears in the above-identified patent and that said Letters Patent is hereby corrected as shown below:

Title Page, Item (54), delete "'FROSTY YOCHERYL" and insert --'FROSTY YOCHERYL'--

Signed and Sealed this
Twenty-sixth Day of April, 2011

David J. Kappos

David J. Kappos
*Director of the United States Patent and Trademark Office*